United States Patent
Williams

(12) 
(10) Patent No.: US 8,984,766 B2
(45) Date of Patent: Mar. 24, 2015

(54) BOOT AND GLOVE DRYER FOR FOOD SERVICE INDUSTRY AND METHOD OF MAKING SAME

(71) Applicant: Gary Williams, Langley (CA)

(72) Inventor: Gary Williams, Langley (CA)

(73) Assignee: Williams Boot & Glove Dryers Inc., Langley, BC (CA)

( * ) Notice: Subject to any disclaimer, the term of this patent is extended or adjusted under 35 U.S.C. 154(b) by 332 days.

(21) Appl. No.: 13/735,254

(22) Filed: Jan. 7, 2013

(65) Prior Publication Data

US 2013/0185951 A1    Jul. 25, 2013

Related U.S. Application Data

(63) Continuation-in-part of application No. 12/797,648, filed on Jun. 10, 2010, now abandoned.

(60) Provisional application No. 61/235,129, filed on Aug. 19, 2009.

(51) Int. Cl.
   *F26B 20/00*    (2006.01)
   *A47L 23/20*    (2006.01)
   *A61L 2/22*     (2006.01)

(52) U.S. Cl.
   CPC ............ *F26B 20/00* (2013.01); *Y10T 29/49826* (2015.01); *A47L 23/205* (2013.01); *A61L 2/22* (2013.01); *A61L 2202/16* (2013.01)
   USPC ................................................. 34/381; 34/60

(58) Field of Classification Search
   CPC ............... F26B 3/00; F26B 5/00; F26B 20/00
   USPC .................. 34/380, 381, 60, 80, 90, 201, 210
   See application file for complete search history.

(56) References Cited

U.S. PATENT DOCUMENTS 1,074,888 A * 10/1913 McIver ............................ 34/104
1,969,953 A *  8/1934 Swartz .............................. 34/79

(Continued)

FOREIGN PATENT DOCUMENTS

CA    2150002 A1    6/1994
EP    380433        8/1990

(Continued)

OTHER PUBLICATIONS

European Search Report for EP 10 17 0969, Date of Completion Oct. 23, 2013, Munich, Germany, 4 pages.

*Primary Examiner* — Steve M Gravini
(74) *Attorney, Agent, or Firm* — Fay Sharpe LLP

(57) ABSTRACT

A rack of the type for circulating air interiorly for drying multiple pairs of boots and/or gloves, where the articles to be dried are sprayed with a liquid sterilizing agent while on the rack. The blower housing, manifold and hollow members of the rack have no exterior horizontal surfaces to prevent pooling of the sterilizing agent. In addition, drain holes are provided in the blower housing, rack tubes and manifold to prevent interior trapping of sterilizing agent or moisture from condensation. In one version intended for sterilizing with power connected, a conduit in the manifold drains any liquid in the blower housing directly into the rack tubes. Another lower cost version is intended for sterilizing after electrical power has been externally disconnected and has liquid/moisture drain holes in the blower housing. Either version may be wall mounted or arranged as portable free standing single or double sided rack drying systems.

18 Claims, 10 Drawing Sheets

(56) References Cited

U.S. PATENT DOCUMENTS

| | | | | |
|---|---|---|---|---|
| 3,078,526 A | * | 2/1963 | Caruso | 422/186 |
| 3,417,482 A | * | 12/1968 | Peet | 34/104 |
| 3,513,564 A | | 5/1970 | Gramprie | |
| 3,798,788 A | * | 3/1974 | Kuntz | 34/104 |
| 4,136,464 A | * | 1/1979 | Hay | 34/104 |
| 4,200,993 A | * | 5/1980 | Blanc et al. | 34/104 |
| D272,644 S | * | 2/1984 | Warren et al. | D32/1 |
| 5,222,308 A | | 6/1993 | Barker et al. | |
| 5,379,525 A | | 1/1995 | Raynor | |
| 5,406,717 A | | 4/1995 | Dofka | |
| 5,412,928 A | | 5/1995 | Reithel | |
| 5,546,678 A | | 8/1996 | Dhaemers | |
| 5,778,556 A | * | 7/1998 | Ohsugi | 34/106 |
| 5,894,680 A | * | 4/1999 | Dalvy et al. | 34/437 |
| D412,231 S | | 7/1999 | Williams et al. | |
| 5,953,830 A | * | 9/1999 | Jannach | 34/104 |
| 5,987,773 A | * | 11/1999 | Lipscy | 34/106 |
| 6,005,227 A | | 12/1999 | Pappas | |
| 6,131,303 A | * | 10/2000 | Roper | 34/90 |
| 6,216,887 B1 | | 4/2001 | Soo | |
| D487,831 S | | 3/2004 | Savoie | |
| 6,742,276 B1 | * | 6/2004 | Anderson et al. | 34/204 |
| 6,766,594 B2 | | 7/2004 | DuRapau | |
| 6,796,053 B2 | | 9/2004 | Lurie | |
| 6,880,711 B2 | | 4/2005 | Collier | |
| 7,083,055 B1 | | 8/2006 | Ambrosat | |
| D615,715 S | * | 5/2010 | Zielinski | D32/8 |
| 2004/0068888 A1 | | 4/2004 | Lurie | |
| 2004/0101456 A1 | | 5/2004 | Kuroshima et al. | |
| 2005/0097768 A1 | | 5/2005 | Burns, Sr. et al. | |
| 2005/0204579 A1 | | 9/2005 | Rosseau et al. | |
| 2006/0124120 A1 | * | 6/2006 | Gross | 126/25 B |
| 2009/0241268 A1 | | 10/2009 | Yoo et al. | |
| 2011/0041354 A1 | * | 2/2011 | Williams | 34/239 |
| 2012/0186098 A1 | * | 7/2012 | Williams | 34/240 |
| 2013/0185951 A1 | * | 7/2013 | Williams | 34/60 |
| 2013/0185953 A1 | * | 7/2013 | Williams | 34/239 |
| 2014/0338212 A1 | * | 11/2014 | Williams | 34/104 |

FOREIGN PATENT DOCUMENTS

| | | |
|---|---|---|
| EP | 0 479 241 A1 | 4/1992 |
| EP | 0 516 563 A1 | 12/1992 |
| EP | 0380433 B1 | 3/1993 |
| EP | 1 369 076 A1 | 6/2003 |
| EP | 2 752 145 A2 * | 7/2014 |
| FR | 2702345 A1 | 9/1994 |

* cited by examiner

BOOT AND GLOVE DRYER FOR FOOD SERVICE INDUSTRY AND METHOD OF MAKING SAME

This application is a Continuation-in-Part of U.S. application Ser. No. 12/797,648, filed Jun. 10, 2010 entitled "Boot and Glove Dryer for Food Service Industry and Method of Making Same," by Gary Williams, and claims the benefit of priority to U.S. Provisional Application No. 61/235,129, filed Aug. 19, 2009, entitled "Boot and Glove Dryer for Food Service Industry," by Gary Williams, and which are hereby incorporated by reference in their entirety.

BACKGROUND

The present disclosure relates to forced air dryer systems for rack drying boots and gloves, and particularly, to such devices in which the rack is either wall mounted or free standing and readily moveable for simultaneous drying of several pairs of boots and/or gloves from a common blower system. Such forced air type dryers are often employed for drying boots utilized in the construction industries and/or boots and gloves for uniformed emergency responders such as for hazardous waste disposal and fire fighters. Upon removal, the user may hang the boots and/or gloves on the rack and the forced air system circulates air to the interior of the gloves and/or boots and, over a period of a few hours, the interior is completely dried. If accelerated drying is required, a heater may be employed with the blower to circulate heated air interiorly of the gloves and/or boots.

In the food service industry including food processing, where workers are required to wear sterilized boots and gloves, it is required that the boots and gloves be sprayed with liquid sterilizing or disinfecting agent, such as bleach, prior to drying. The presence of the liquid sterilizer must be controlled such that pooling or residual amounts of liquid sterilizer are not retained on any horizontal surface such that bacteria could be collected over a time interval prior to total evaporation or drying of the sterilization liquid. In this regard, it has been found beneficial to provide for rack mounting of the boots/gloves to optimize the sterilization process and prevent contamination.

Accordingly, it has been desired to provide a way or means of air drying boots and/or gloves requiring sterilization with forced air circulation interiorly thereof in a manner and with equipment that prevents liquid pooling and completely drains of any sterilizer. It has been particularly desired to provide a system in a wall rack version and a free standing portable rack version capable of drying a multiple number of pairs of boots and/or gloves which require sterilization without trapping any of the sterilizing liquid exteriorly on or interiorly of the air drying system.

BRIEF DESCRIPTION

The present disclosure describes a system including a rack for receiving multiple pairs of boots and/or gloves with a blower for circulating air interiorly of the gloves and/or boots for effecting interior drying thereof in which the boots and/or gloves are subject to sterilization with a sterilizing agent sprayed thereon when mounted on the rack. The blower system and the hollow members of the rack are configured such that there is a complete absence of exterior horizontal surfaces and that pooling of the sterilizing agent does not occur on any non-vertical interior or exterior surfaces. In addition, the interior surface of the rack tubes are provided with strategically located drain holes such that the sterilizing agent or moisture from condensation, upon entering the interior of any of the blower housing, air distribution manifold, distribution tubes or boot/glove holding tubes, is completely drained to prevent trapping or pooling of the sterilizing agent. One disclosed version is intended for sterilizing with electrical power connected; and, another version is disclosed which is intended for sterilizing only after electrical power has been externally switched off. Both versions are adapted for wall mounting or alternatively may be arranged as free standing portable single or double sided rack drying systems.

DETAILED DESCRIPTION

Figure 1:
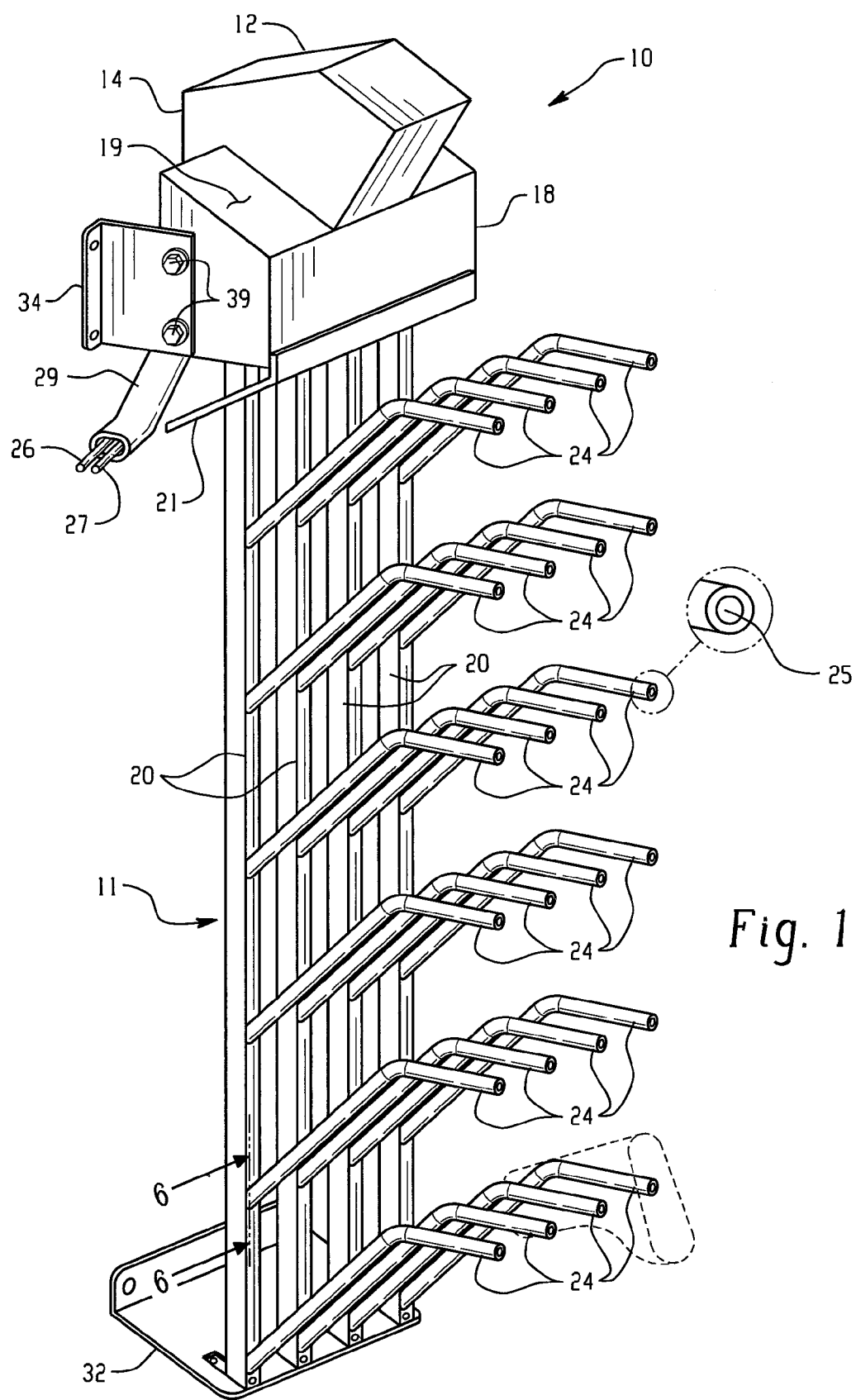
FIG. 1 is a perspective view from the front of a wall mounted version of the forced air drying system and rack for multiple pairs of boots and/or gloves according to the present disclosure.
Figure 2:
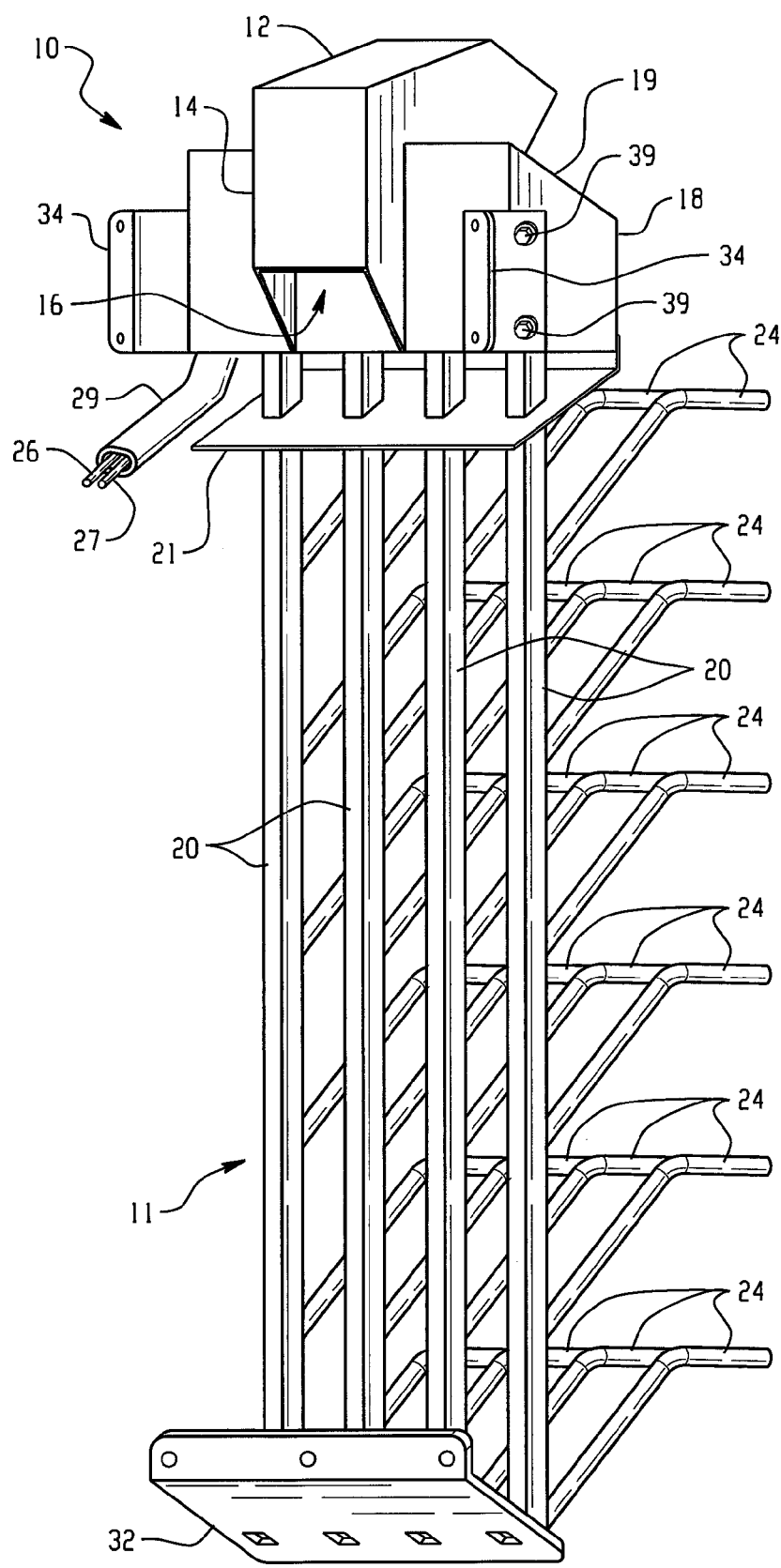
FIG. 2 is a perspective view from the back of the version of FIG. 1.
Figure 3:
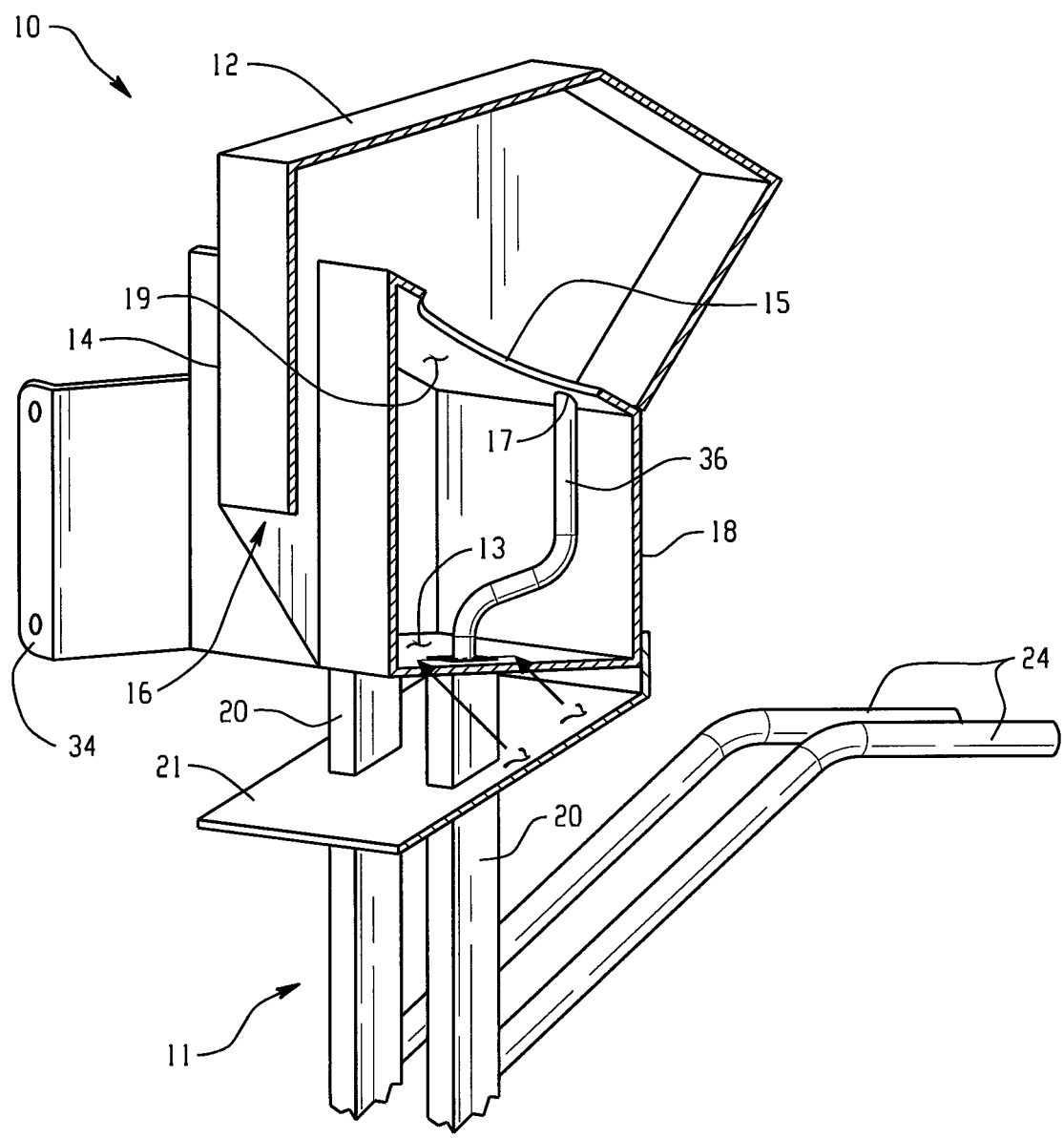
FIG. 3 is an enlarged view of FIG. 2 with portions broken away to illustrate the interior of the blower housing and air distribution manifold of the system of FIG. 1.
Figure 7:
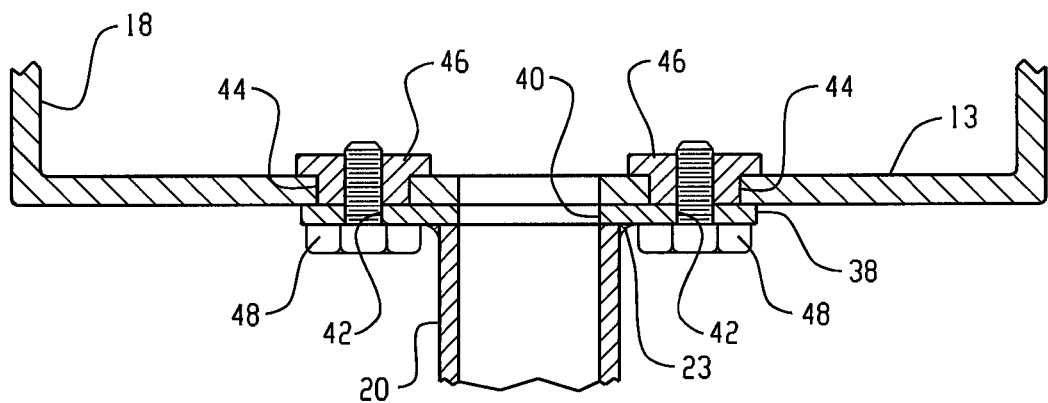
FIG. 7 is a section view taken along section-indicating lines 7-7 of FIG. 3.

Referring to FIG. 1, a forced air drying system for drying the interior of multiple pairs of boots or gloves is shown generally at 10 as adapted to be mounted on a wall or vertical surface panel for accommodating multiple pairs of boots and/or gloves for simultaneous drying. The system 10 includes a blower housing 12 having, disposed interiorly thereof, a suitable blower (not shown); and, the housing 12 has a portion thereof overhanging and extending downwardly along the back side of an air distribution manifold 18. If desired, an unshown heater may be incorporated within the blower housing 12. Blower housing 12 sits atop a sloping upper surface 19 of the air distribution manifold 18; and, the surface 19 has openings therein such as 15 (see FIG. 3) for enabling forced air from the blower to enter the manifold. As shown in FIGS. 2 and 3, the lower end of overhanging portion 14 of the blower housing is open and forms the air inlet indicated generally at 16 for the blower housing. Manifold 18 has a rack indicated generally at 11 with a plurality of distribution tubes 20 connected to the underside of the floor 13 of manifold 18, which tubes 20 extend downwardly therefrom in spaced generally parallel arrangement. As shown typically in FIG. 3 and FIG. 7, the interior of each of the distribution tubes 20 is open to the interior of the manifold 18 permitting air in the manifold to enter each of the distribution tubes 20. Tubes 20 may be attached to the manifold by any suitable expedient such as shown in FIG. 7, wherein a flange 38 is attached to the end of distribution tube 20, such as for example by weldment, the flange having aperture 40 conforming to the interior of tube 20. The flange 38 has a plurality of fastener receiving apertures 42 disposed about aperture 40. The manifold floor 13 has correspondingly located apertures 44 into which are pressed threaded nuts 46 such as for example T-nuts. If desired, the T-nuts may be additionally secured such as by staking or weldment. The tubes are then secured by threaded fasteners 48 engaging nuts 46 through apertures 42 in flange 48.

As shown in FIG. 3, the interior of the manifold has at least one discrete drain conduit in the form of tube 36 vertically oriented such that its upper end communicates with a drain hole 17 formed in the sloping surface 19 of the manifold; and, tube 36 is configured such that the lower end of drain tube 36 is oriented to discharge into one of the distribution tubes 20 for draining the blower housing directly into the rack tubes. In operation, as air if forced into the manifold and down the tubes 20, an aspirating effect is created on the lower end of tube 36, thus facilitating draining of any liquid in the blower housing 12.

FIGS. 1 and 3 illustrate further detail of the system 10 which has the blower housing disposed such that the upper surface thereof is sloped thereby providing a housing with no horizontal surfaces which could trap or pool sterilizer or disinfectant sprayed over the system. As shown in FIGS. 1-3, the manifold may have an optional splash guard 21 attached thereto and angled downwardly under the manifold.

Figure 6:
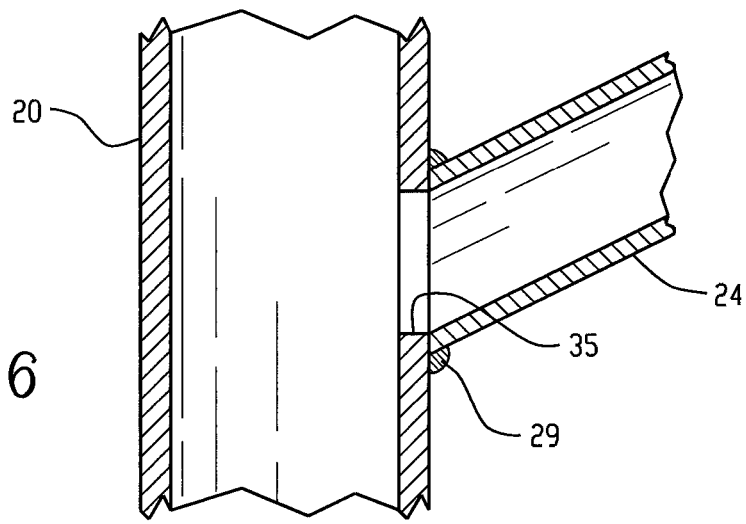
FIG. 6 is a section view taken along section-indicating lines 6-6 of FIG. 1.

The version of FIGS. 1-3 is thus intended to protect the blower system from liquid entry where electrical power is being supplied to the blower during spraying of liquid sterilizer/disinfectant Each of the distribution tubes 20 has at least one, and preferably a plurality, of boot/glove hanging tubes or tubular support arms for articles to be dried extending outwardly therefrom in cantilever as denoted by reference numerals 24 in FIGS. 1-3. In the present practice, it has been convenient to have the distribution tubes 20 formed with a rectangular or square cross section to facilitate attachment of the hanging tubes 24. In one exemplary version of the present forced air drying system, it has been found satisfactory to form the distribution tubes 20 of square tubing having a side width of 1.5 inches (38 mm) and the hanging tubes 24 of 1.0 inch (25 mm) diameter round tubing; however, other cross sections and sizes may be employed. As shown typically in FIGS. 3 and 6, each of the tubes 24 has one end thereof attached to one of the distribution tubes 20; and, each of the tubes 24 has the interior thereof open to the interior of the distribution tube 20 through an orifice 35 formed in the wall of the distribution tube 20, to provide fluid communication therewith such that air forced into the tubes 20 is also forced into the tubes 24 and out through the open end of each of the tubes 24. Tubes 24 may be attached to the tubes 20 by any suitable expedient such as by weldment 29 shown in FIG. 6.

Referring to the enlarged encircled view in FIG. 1, in the present practice, it has been found desirable to provide an appropriately sized air flow choke orifice 25 in the end of each hanging tube 24 to balance airflow throughout the rack. The choke orifices may be conveniently formed in plastic inserts provided in the ends of the tubes 24. The plastic inserts forming the orifices 25 may be configured for ready removal and replacement as may be required to provide additional protection against contamination. It will be understood that the open end of a boot is received for drying over the tube with the toe portion of the boot hanging downwardly as illustrated in dashed outline in FIG. 1.

Referring to FIGS. 1 and 2, the unshown blower disposed within the housing 14 is adapted for connection to a source of electrical power by suitable electrical leads such as leads 26, 27 encased in suitable insulation to form a power cord 29. For food processing applications of the system of FIG. 1 in which sterilization is required, it will be understood that the connection of power cord 29 to the manifold, blower housing and blower must be sealed against liquid penetration, which sealing may be accomplished in any convenient known manner. The system of FIGS. 1 and 2 is thus intended for operation where the sterilizing will be performed with electrical power connected to the system; and, if desired, while the blower is in operation.

Figure 8:
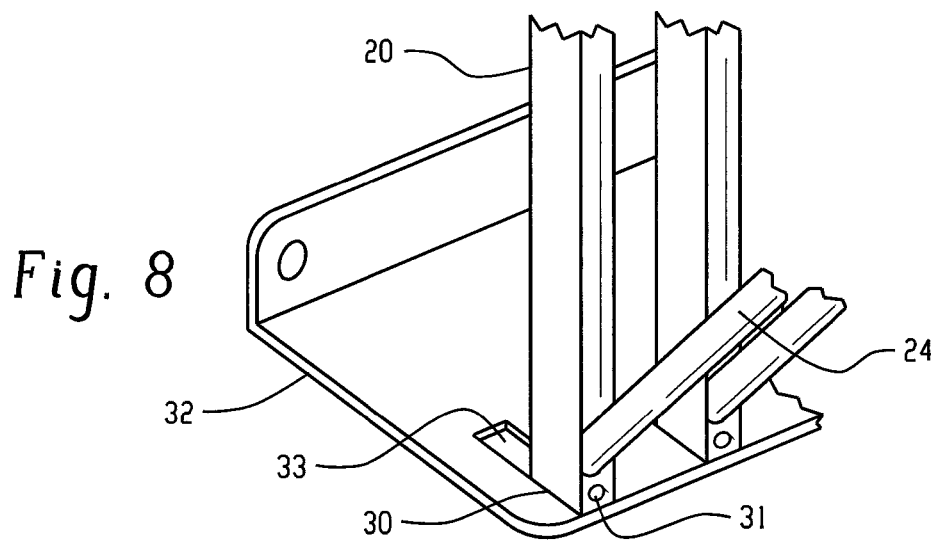
FIG. 8 is an enlarged view of the lower end portion of a distribution tube of FIG. 1.

Referring to FIG. 8, one of the vertical distribution tubes 20 is shown with one of the boot/glove hanging tubes 24 attached thereto near the lower end of the distribution tube 20. FIG. 8 illustrates the angled closed end 30 of the tube 20 such that any liquid entering the tube 20 drains to the lowest point of the angled surface. Drain holes 31 are provided at the lowest point of the surface 30 of each tube 20 to drain any liquid entering the distribution tube 20 from the manifold or from the tubes 24. Cut outs 33, which may be punched in bracket 32, prevent trapping or buildup of liquid behind distribution tubes 20.

Referring to FIG. 1, the system 10 as shown is adapted to be anchored to a wall or vertical panel at the lower end of the tubes 20 by a suitable bracket 32 and by at least one bracket 34 at the blower manifold 18. In the present practice, it has been found satisfactory to provide wall mounting surfaces such as a bracket 34 attached on each opposite side of the manifold 18 as shown in FIG. 2 for example by bolts 39 to the wall of the manifold. Alternatively, the wall mounting surfaces may be integrally formed with the manifold. Although the system 10 has been shown mounted on a wall, alternatively, it may be mounted to a free standing pedestal if desired, as will be hereinafter described. In the present practice, it has been found satisfactory to form the blower housing 14, manifold 18, distribution tubes 20 and hanging tubes 24 of stainless steel, however, other corrosion resistant materials could be used.

Figure 4:
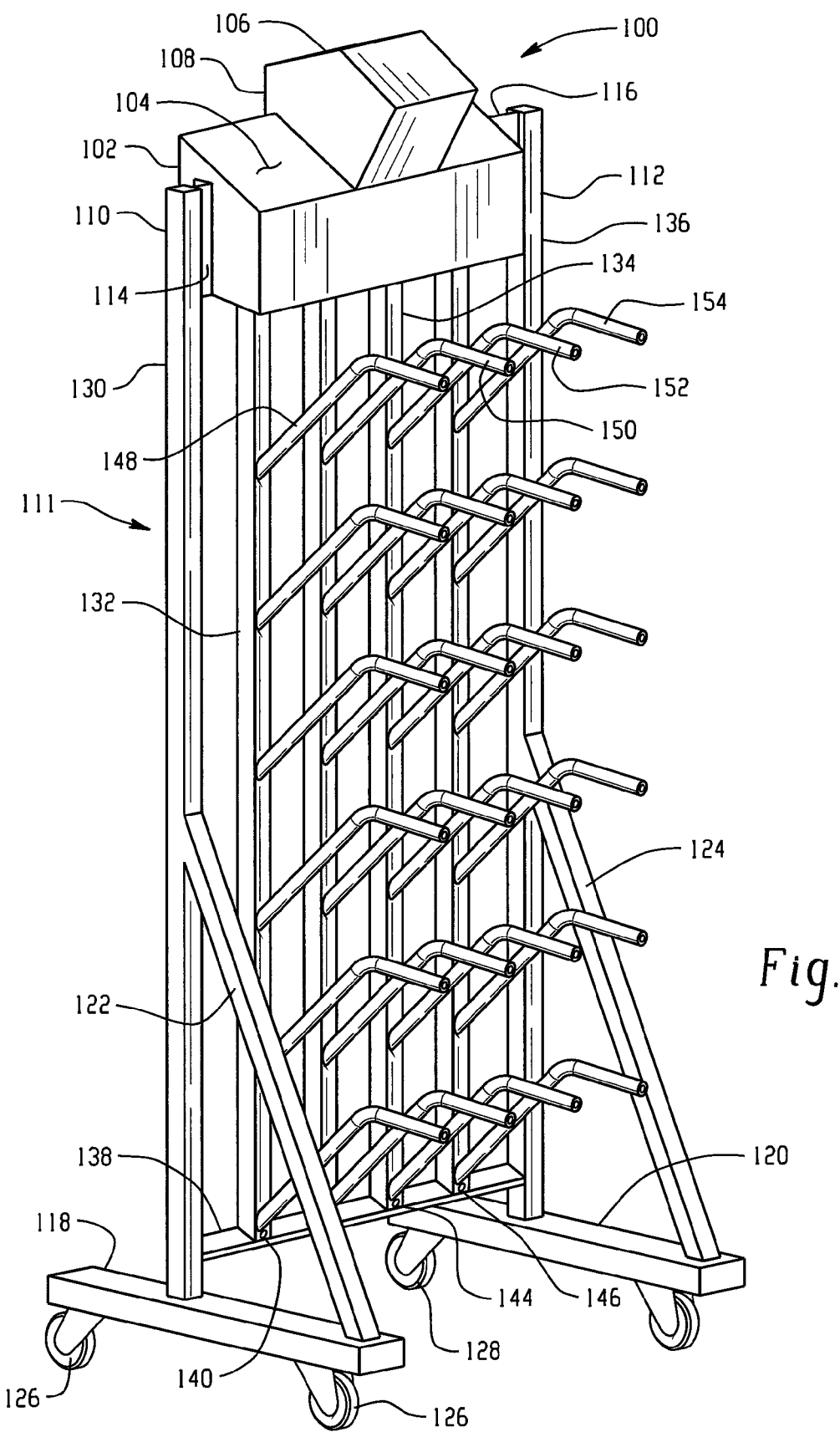
FIG. 4 is a perspective view of a free standing single sided rack portable version of the present forced air drying system.

Referring to FIG. 4, another version of the forced air drying system is indicated generally at 100 and has a manifold 102 with sloping upper surface 104 having a blower housing 106 mounted thereon with a rearward overhanging portion 108 provided thereon for forming an air inlet in a manner similar to air inlet 16 of the FIG. 1 version. Manifold 102 is supported on opposite sides thereof by posts 110, 112 which may comprise tubular members or channels and which may be attached to the manifold by attachment brackets 114, 116 by any suitable expedients such as weldment or fasteners. It will be understood that sloping upper surface 104 of the manifold 102 is provided with an unshown drain similar to drain 17 and also provided with an air passage similar to passage 15.

Posts 110, 112 are supported at their lower end on horizontal support or beam members 118, 120 and maintained positioned vertically by diagonal braces 122, 124, respectively. In the present practice, it has been satisfactory to form the posts, braces and horizontal beam members of tubular configuration to minimize the weight of the assembly. Horizontal beam members 118, 120 upon which posts 110, 112 are supported may each have rollers 126, 128, respectively, mounted on the undersurface thereof at opposite ends to permit the entire assembly to be rolled about and thus rendered portable. If desired, at least a pair of the rollers may be swiveled or castored.

The manifold 102 has attached to the undersurface thereof and extending downwardly therefrom a rack indicated generally at 111 which includes a plurality of spaced generally parallel tubular members 130, 132, 134, 136. The manifold has apertures formed therein (unshown) such that the tubular members 130, 132, 134, 136 each have the interior thereof fluidically communicating with the interior of manifold 102 in a manner similar to that of FIGS. 3 and 7. The lower end of each of the distribution tubes 130, 132, 134, 136 is sloped and has a sloped cross-member 138 attached thereto for closing the lower end of the distribution tubes 130, 132, 134, 136. Drain holes 140, 142, 144, 146 are provided in the lower edge of each of the distribution tubes 130, 132, 134, 136 for draining moisture therefrom. Each of the distribution tubes 130, 132, 134, 136 has provided thereon extending generally upwardly and outwardly in cantilevered arrangement a plurality of hanging tubes denoted 148, 150, 152, 154, respectively. Each of the hanging tubes has an appropriately sized choke orifice provided in the free end thereof sized to equalize the flow of air throughout the distribution tubes and hanging tubes. In the present practice it has been found satisfactory to form the choke orifices in removable and replaceable inserts, which may be formed of plastic material provided in the ends of the hanging tubes. In the present practice, it has been convenient to form the manifold, blower housing, posts, distribution tubes, hanging tubes and structural support members of stainless steel or other corrosion resistant material. The attachment of the hanging tubes to the distribution tubes and the attachment of the distribution tubes to the manifold may be accomplished by any suitable expedient; a, for example, by welding or brazing.

Figure 5:
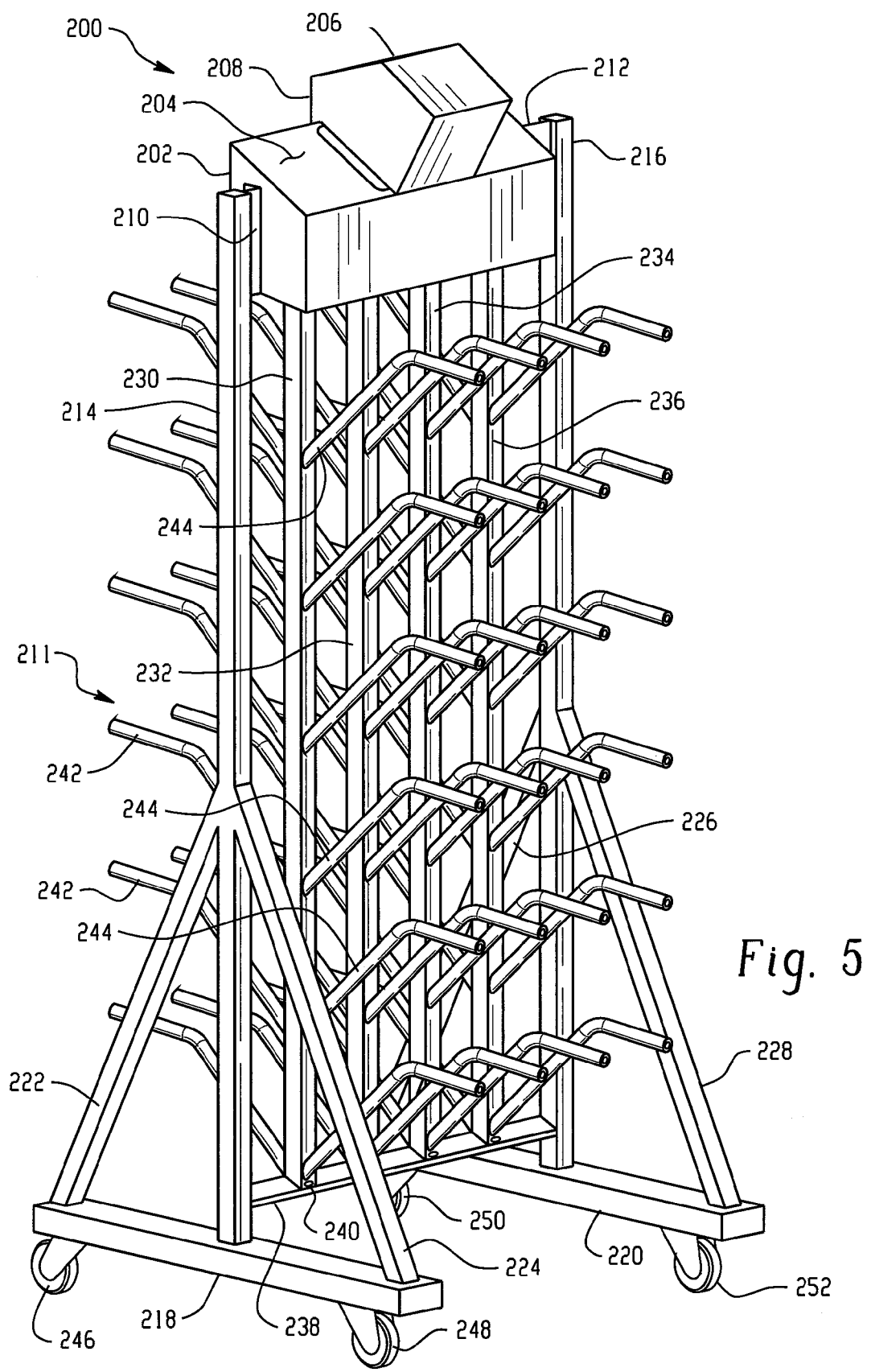
FIG. 5 is a perspective view of a free standing double sided rack portable version of the present forced air drying system.

Referring to FIG. 5, another version of a free standing portable drying system in accordance with the present disclosure is indicated generally at 200 and has a manifold 202 with sloping upper surface 204 having mounted thereon a blower housing 206. Housing 206 has a rearward overhanging portion 208 which forms an air inlet; and, housing 206 has enclosed therein an unshown blower which may include a heater, if desired. Manifold 202 has attached to the opposite sides thereof mounting brackets 210, 212, each of which is attached to and supported by a vertical post 214, 216, respectively, which posts may conveniently be formed of square tubing. Posts 214, 216 are each supported at its lower ends by horizontal support members in the form of beams 218, 220, respectively; and, diagonal braces 222, 224, 226, 228 are provided to position and maintain the posts vertically aligned. The posts, braces and horizontal beam members may be conveniently formed of tubular or channel stock for minimizing weight.

The manifold 202 has extending downwardly from the under surface thereof, a plurality of spaced generally parallel distribution tubes 230, 232, 234, 236 which have the lower ends thereof sloped and attached to a sloped cross-member 238 which closes the lower end of each of the distribution tubes and is attached at its opposite ends to the posts 214, 216, respectively. Each of the distribution tubes 230, 232, 234, 236 has a drain hole, such as hole 240 in tube 230, at its lower edge for draining any interior moisture.

Each of the distribution tubes 230, 232 has a plurality of hanging tubes 242 connected thereto and extending in cantilever therefrom on a common face thereof; and, each of the distribution tubes 230, 232 also has a second plurality of hanging tubes 244 connected thereto and extending in cantilever therefrom on the opposite side of the distribution tubes 230, 232 to thereby form a double sided rack for hanging boots and gloves thereon for drying. Each of the hanging tubes 232, 234 has an airflow choke orifice provided in the end thereof in a manner similar to that of the embodiment of FIG. 1.

The supporting structure, shown in the form of horizontal beam members 218, 220 may be optionally provided on the opposite ends thereof with rollers 246, 248 and 250, 252 which may be swiveled or castored if desired, to permit portability of the assembly 200. In the present practice, it has been found satisfactory to form the manifold, blower, housing, rack tubes and tubular support structure of stainless steel or other corrosion resistant material.

Figure 9:
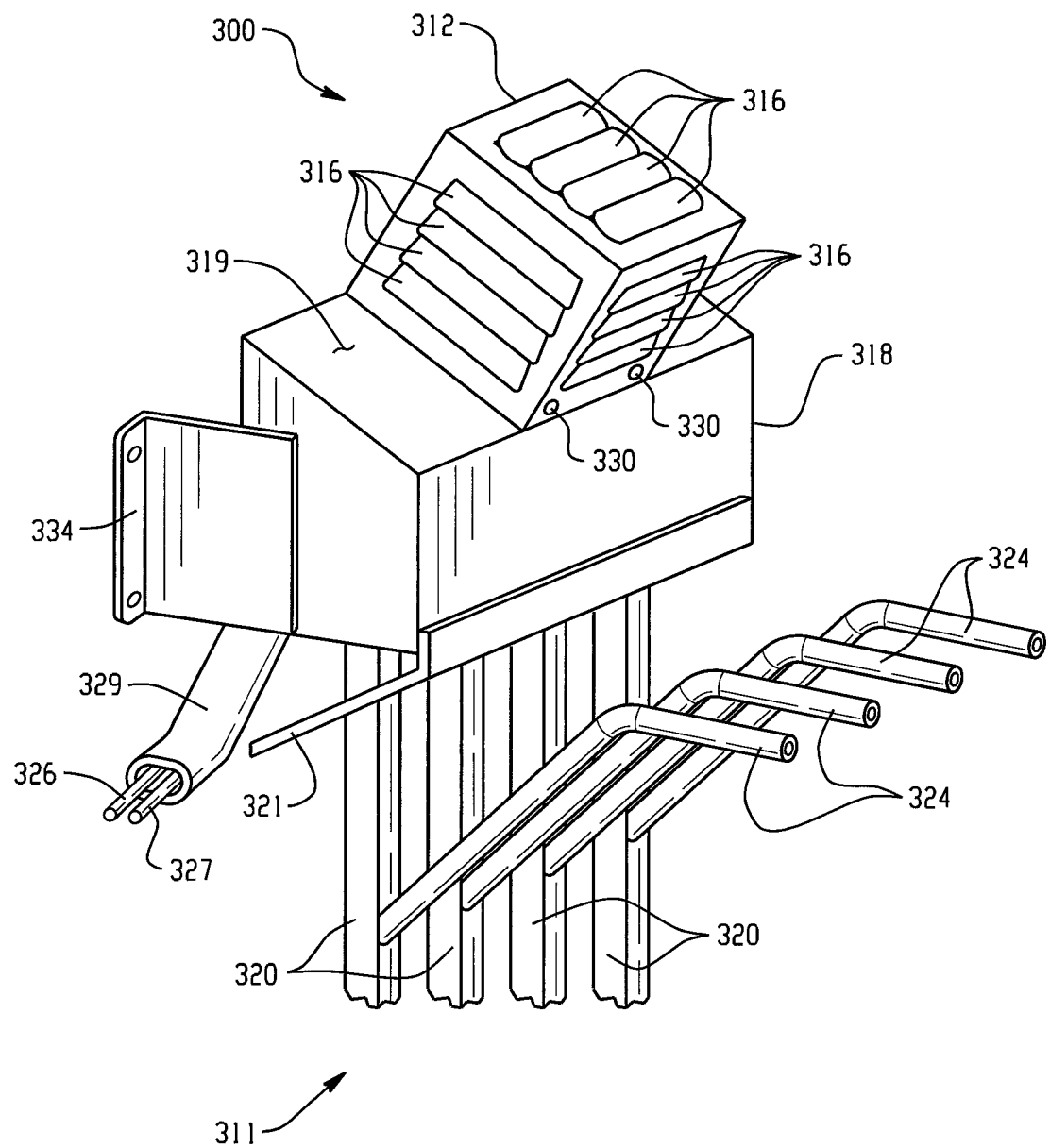
FIG. 9 is a portion of a view similar to FIG. 1 showing another version with a louvered enclosed blower housing.

Referring to FIG. 9, another version of the drying system of the present disclosure is indicated generally at 300 which is intended for spraying of sterilizing liquid only with electrical power externally switched off or disconnected. The system 300 has a rack indicated generally at 311 extending downwardly from the undersurface of an air manifold 318 which has a sloped upper surface 319 upon which is mounted a blower housing 312 for housing an unshown blower. The sloping upper surface 319 of the air manifold 318 is intended to have an air flow aperture, although unshown, similar to the aperture 15 of FIG. 3 to permit forced air from blower housing 312 to enter the manifold 318.

The blower housing 312 has its inlet provided by a plurality of louvered vents 316 provided on the sides and upper surface of the blower housing. The manifold is adapted for attachment to vertical surface by the brackets, one of which is shown at 334. The rack 311 comprises a plurality of vertically downwardly extending riser tubes 320, each of which has a boot/glove hanging tube 324 cantilevered therefrom. The manifold is provided with power through cord 329 having therein electrical leads 326, 327, it being understood that the entrance of the power cord 329 to the manifold is sealed to prevent water penetration.

An optional splash shield 321 is angled downwardly from the front edge of the manifold and has cutouts for the risers 320 such that the splash shield can extend behind the risers.

At least one and preferably a plurality of drain holes 30 are provided in the front face of the blower housing 312 at the lowest edge thereof for permitting any liquid entering the blower housing to drain to the exterior. Thus, the version of FIG. 9 is somewhat simpler in construction inasmuch as the interior drain tubes from the blower housing to the risers is omitted and the rearward overhang is eliminated. However, the version of FIG. 9 is intended for use only where electrical power to the power cord 329 is disconnected exteriorly during the spraying of liquid sterilizer/disinfectant on the articles hanging on the rack.

Although the system 300 of FIG. 9 is illustrated as wall mounted, it would be understood that the system may also be configured as free standing in a manner similar to the versions shown in FIGS. 4 and 5.

Figure 10:
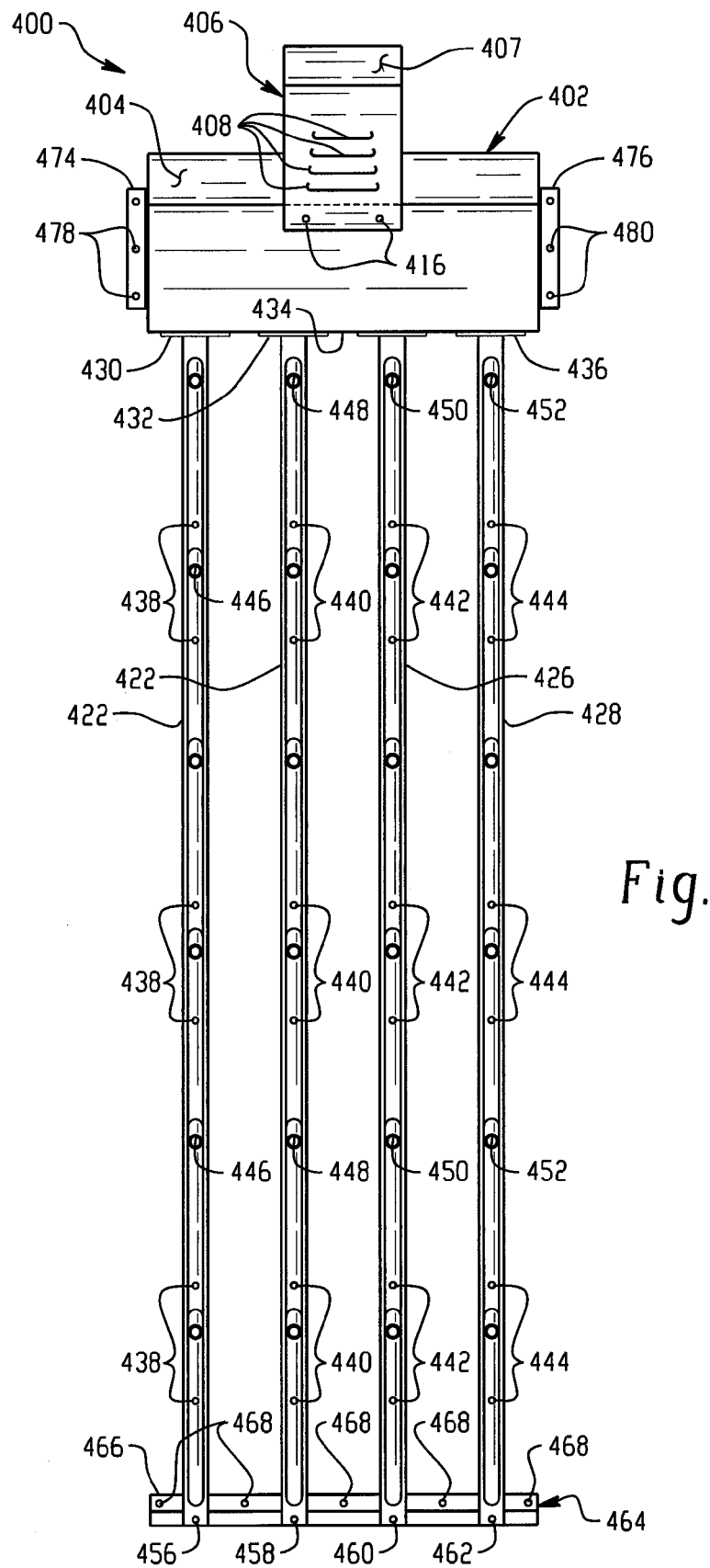
FIG. 10 is a front view of another version of the dryer system of the present disclosure for wall mounting.
Figure 11:
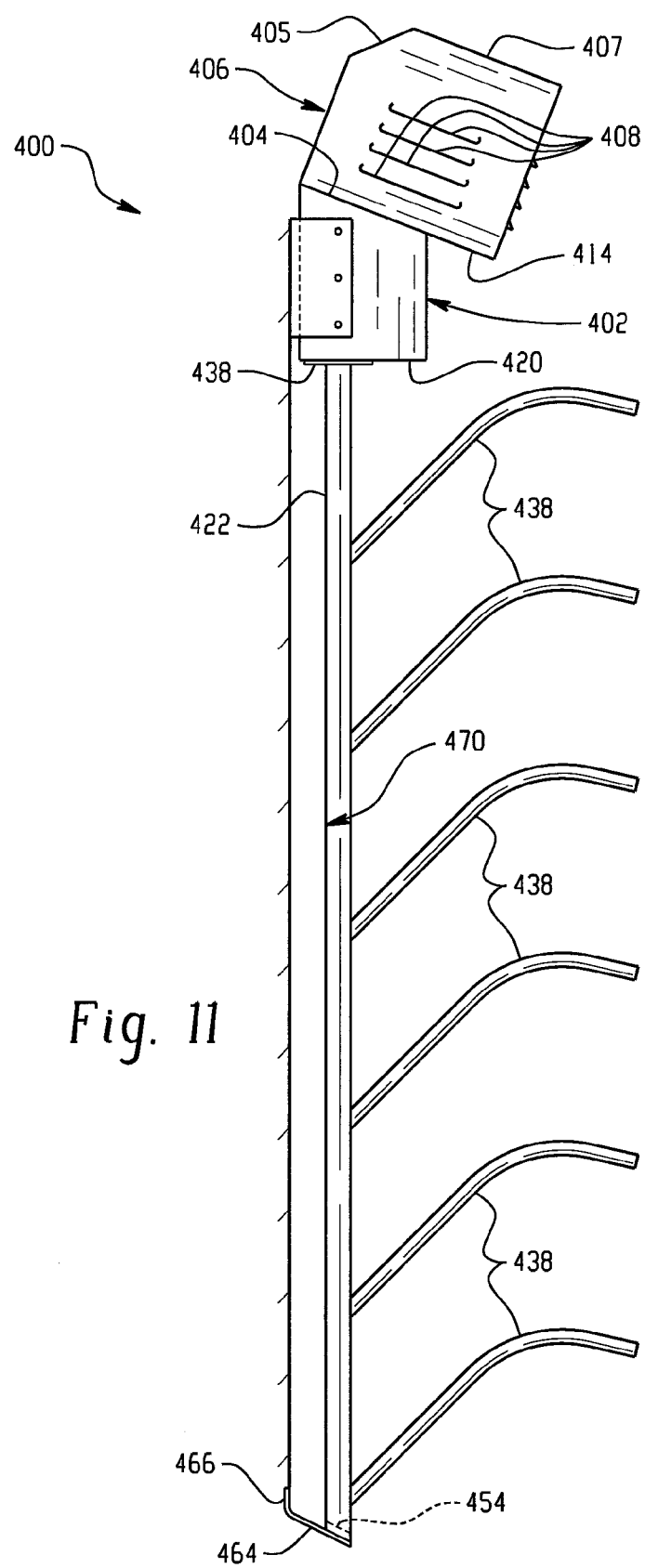
FIG. 11 is a left side view of the version of FIG. 10.
Figure 12:
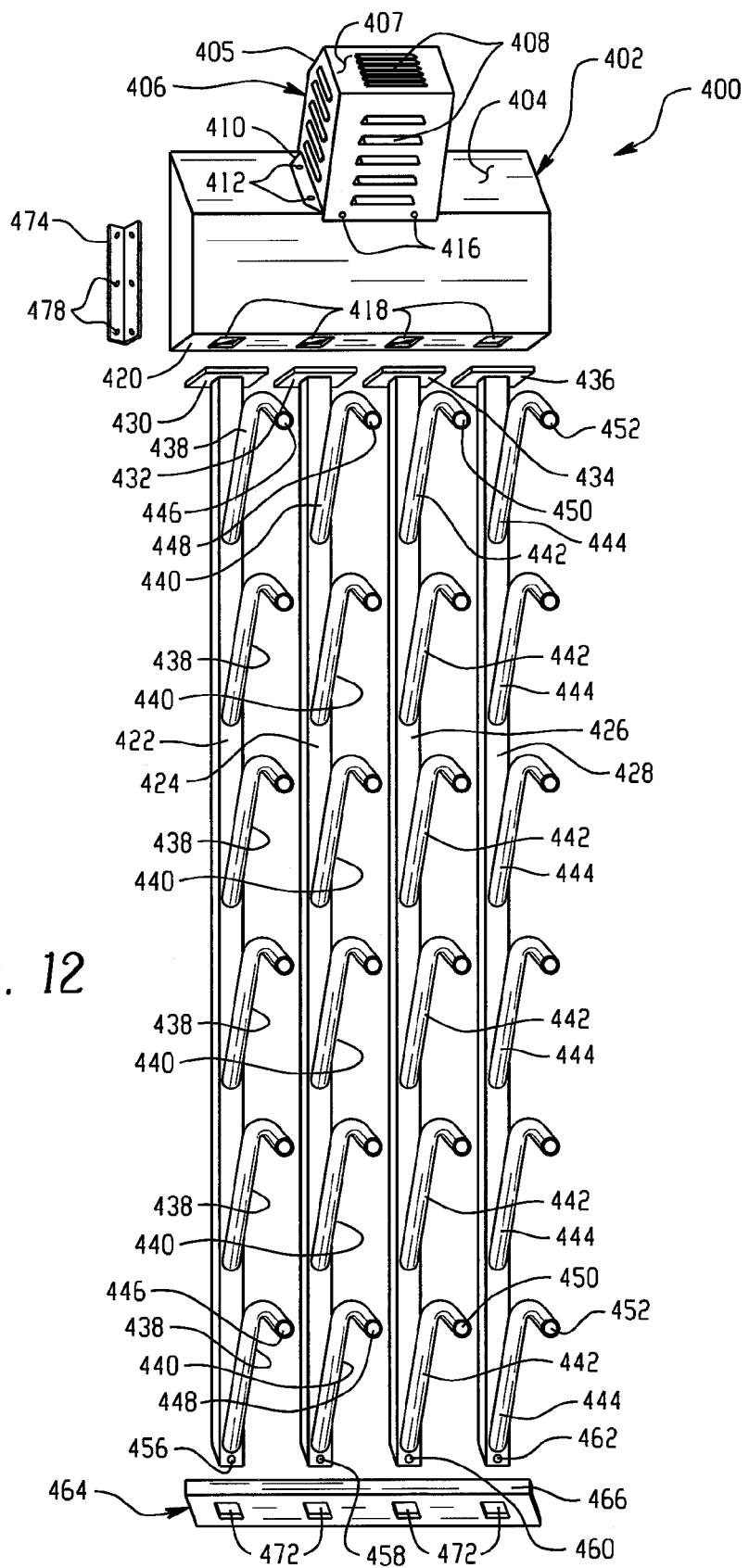
FIG. 12 is a perspective view from the front of the version of FIG. 12 in the disassembled condition.

Referring to FIGS. 10-12, another version of the system for drying boots and/or gloves being sprayed with disinfectant is indicated generally at 400 and has an air manifold indicated generally at 402 having a sloped upper surface 404 upon which is mounted a blower housing indicated generally at 406 with air inlets 408. It will be understood that the housing 406 has contained therein an unshown blower and has unshown sealed electrical leads similar to the version 10 of FIGS. 1 and 2. The housing 406 may have flanges such as flange 410 provided on opposite sides thereof for facilitating attachment to the blower housing as, for example, by screws 412. It will be understood that the blower housing 406 is received over an unshown aperture in the upper surface 404 for providing a flow of forced air to the interior of the manifold 402.

The blower housing 406 has a portion 414 thereof disposed to overhang the side or front face of the manifold 402 such that the lowest portion 414 of the lower housing is not disposed directly over the manifold. This arrangement serves the purpose of collecting moisture in the portion 414 and preventing the moisture from entering the forced air aperture between the blower housing and the manifold. As shown in FIGS. 10-12, the upper surfaces 405, 407 of the blower housing 406 are also sloped for drainage. In furtherance of this purpose, eferring to FIGS. 10 and 12, the wall or face of the blower housing adjacent the lowest margin of the overhanging portion 414 has provided therein threadable drainage holes denoted by reference numeral 416.

Referring to FIG. 12, the lower surface 420 of the manifold 402 has a plurality of spaced air discharge apertures 418 spaced therealong. Attached to the lower surface 420 of the manifold 402 is a plurality of spaced generally parallel tubular distribution members 422, 424, 426, 428, each of which has a mounting flange 430, 432, 434, 436 attached respectively thereto at its upper end such as by weldment. It will be understood that each of the mounting flanges has a central aperture (not shown) formed therein for providing communication of forced air from apertures 418 with the interior of the respective distribution members 422-428.

The flanges 430-436 are each, respectively, attached to the undersurface 420 of the manifold either releasably with screws (not shown) or permanently by weldment such that one of the apertures 418 is aligned with the aperture in the flange to provide communication of forced air from the manifold into the interior of the respective tubular distribution member 422-428. The distribution arms 422-428 each have a plurality of tubular article support arms 438, 440, 442, 444, respectively, spaced therealong and extending outwardly therefrom in cantilever arrangement for receiving thereover the articles such as boots and/or gloves to be sprayed and dried. Each of the tubular support arms 438, 440, 442, 444 has provided thereon a substantially closed end with an air discharge orifice indicated, respectively, 446, 448, 450, 452, for discharging air to the articles to be dried. It will be understood that the air discharge apertures 446-452 may be formed in removable chokes in a manner similar to that described herein above.

Each of the tubular distribution members 422-428 has the lower end thereof sloped and closed by a suitable closure member or plate such as indicated in dashed line in FIG. 11 and denoted with reference numeral 454. The closure member or plate 454 may be secured in a suitable manner as, for example, weldment or by suitable adhesives. Each of the distribution members 422-428 has provided therein at the lowest portion of the sloped end or at the portion furthest removed from the manifold, a drain aperture denoted respectively 456, 458, 460, 462 in FIG. 12.

A cross piece indicated generally at 464 is attached to the closed, sloped ends of each of the distribution members 422-428 as, for example, by weldment or unshown screws into the closure plate such as plate 454. The cross piece 464 in the embodiment 400 is configured in the form of a bracket having a wall mounting flange 466 which may have suitable apertures such as holes 468 provided therein for receiving suitable fasteners for mounting to a wall indicated generally at 470 in FIG. 11.

Referring to FIG. 12, the cross piece or bracket 464 has a plurality of drainage apertures denoted typically at 472 provided therein and spaced therealong which apertures 472 are each located to be positioned adjacent the edge of the sloped surface on the end of one of the distribution members 422-428 adjacent the wall 470 such that moisture or sterilizer/disinfectant draining down the distribution tube is not trapped on the bracket but is drained therethrough. It will be understood that the apertures 472 are arranged in a manner similar to that of the wall mounting bracket apertures shown and described hereinabove with respect to the version 10 as illustrated in FIG. 8.

The manifold 402 in the version 400 is illustrated as having a pair of mounting brackets 474, 476 provided on opposite ends thereof which brackets are configured with flanges having apertures 478, 480 provided therein for receiving fasteners for attachment to the wall 470. Although the version 400 has been illustrated with mounting brackets 472-476 for wall mounting, it will be understood that the version 400 may be alternatively provided with suitable support structure arranged to maintain the rack free standing in a manner similar to that described hereinabove with reference to the version 200 as shown in FIG. 5.

The version 400, thus, provides a dryer system for boots and gloves for food service processing subjected to spraying of disinfectant/sterilizer with a blower housing attached to the sloped upper surface of the manifold and overhanging the manifold so as to provide drainage of any moisture in the blower housing away from the manifold. The lowerends of the distribution tubes of the rack are provided with sloping end plates; and, drain holes are provided in the lower edge thereof. A cross piece is provided as a bracket for wall mounting and interconnects the lower ends of the distribution tubes. The bracket has apertures therein for preventing pooling on the bracket of liquid sprayed on the distribution tubes.

The present disclosure thus describes a forced air drying system for drying multiple pairs of boots and/or gloves for food processing or other applications where it is required to spray the boots and/or gloves with liquid disinfectant or sterilizing agent prior to or during drying operations while in position on the hanging tubes of the rack. The blower housing, air manifold and distribution tubes are configured such that any horizontal or non-vertical surfaces are eliminated which could result in pooling or trapping of disinfectant or sterilizer either externally on or in conjunction with drain holes interiorly in any of the members of the system. One version is intended for use with electrical power connected and another lower cost version is intended for use with electrical power externally disconnected. The systems in either version may be wall mounted or arranged as free standing single sided or double sided rack portable drying systems.

The exemplary embodiments have been described with reference to the drawings. Obviously, modifications and alterations will occur to others upon reading and understanding the preceding detailed description. It is intended that the exemplary versions disclosed be construed as including all such modifications and alterations insofar as they come within the scope of the appended claims or the equivalents thereof.

The invention claimed is:

1. A forced air drying system for boots and/or gloves for use in food service processing requiring spraying with sterilizer/disinfectant comprising:

(a) a rack having a plurality of spaced tubular distribution members each having a plurality of tubular article support arms having an air discharge orifice extending therefrom for receiving thereon the boots and/or gloves to be sprayed and dried;

(b) a manifold having a sloped upper surface and a lower surface, the lower surface connected to an upper end of each of the tubular distribution members;

(c) a blower housing having an air inlet mounted on the manifold sloped upper surface, the blower housing including a fluid drain and a portion overhanging the manifold; and, wherein interior moisture in the manifold is drained into the tubular distribution members, wherein the ends of the distribution tubes distal the manifold are closed and sloped, each with a drain port adjacent the lowest portion of the sloped end; and, (d) a cross piece connected to the ends of the tubular distribution members distal the manifold.

2. The drying system defined in claim 1, wherein the tubular distribution members are interconnected by a bracket at an end distal the manifold, the bracket having surfaces thereon configured for wall mounting.

3. The system of claim 2, wherein the bracket has a void adjacent each distribution tube, for drainage to prevent moisture pooling adjacent the distribution tube.

4. The system of claim 1, wherein the fluid drain in the blower housing is located in the portion overhanging the manifold.

5. The system of claim 1, wherein the manifold includes at least one wall mounting bracket.

6. The system of claim 1, wherein the manifold includes at least one wall mounting bracket.

7. The system of claim 1, wherein the tubular distribution members have a cross section selected from one of (a) square and (b) rectangular.

8. The system of claim 1, wherein the blower housing, manifold and tubular distribution members are formed of one of (a) stainless steel and (b) corrosion resistant material.

9. The system of claim 1, wherein the blower housing includes electrical leads sealed against liquid penetration.

10. The drying system of claim 1, further comprising support structure connected to the manifold and rack for maintaining the rack in free standing condition.

11. The system of claim 10, wherein the support structure includes rollers for portability.

12. The system of claim 10, wherein the rack includes distribution tubes with article support arms on opposite sides thereof.

13. A method of making a forced air drying system for boots and/or gloves for use in food processing requiring spraying with sterilizer/disinfectant comprising:

(a) providing a rack having a plurality of spaced tubular distribution members each having a plurality of article support arms extending therefrom with a discharge orifice therein for receiving thereon the boots and/or gloves to be dried;

(b) providing an air manifold having a sloped upper surface and a lower surface and connecting the manifold lower surface to an end of each of the tubular distribution members and providing and arranging the manifold for draining interior moisture therein into the tubular distribution members;

(c) disposing a blower housing on the manifold sloped upper surface and configuring a portion of the manifold for overhanging the manifold and providing a drain in the blower housing;

(d) forming closed and sloped ends on the tubular distribution members distal the manifold and forming a drain port in each tubular member adjacent the lowest portion of the sloped end; and, interconnecting ends of the tubular distribution members distal the manifold with a cross piece.

14. The method of claim 13, further comprising providing removable air flow chokes in the free end of each of the tubular support arms and balancing air flow in the rack.

15. The method of claim 13, wherein interconnecting the ends of the tubular distribution members distal the manifold with a cross piece includes providing a bracket for wall mounting.

16. The method of claim 13, further comprising providing support structure connected to the manifold and cross piece and maintaining the rack in free standing arrangement.

17. The method of claim 16, further comprising disposing rollers on the support structure and enabling free standing portability.

18. The method of claim 13, wherein providing a drain in the blower housing includes forming apertures in the portion of the blower housing overhanging the manifold.

* * * * *